United States Patent
Shteingold

[19]

[11] Patent Number: 6,149,550
[45] Date of Patent: Nov. 21, 2000

[54] MUSCLE STRENGTH TESTING APPARATUS

[76] Inventor: David Shteingold, 160 Neptune Blvd., #307 W, Lynn, Mass. 01905

[21] Appl. No.: 09/408,679

[22] Filed: Sep. 30, 1999

[51] Int. Cl.$^7$ .................................................. A63R 23/02
[52] U.S. Cl. ............................ 482/8; 482/901; 482/902; 482/104; 73/379.01
[58] Field of Search ........................... 482/1–9, 900–902, 482/91, 100, 134, 137, 133, 106, 104; 73/379.01–379.03, 379.06, 379.08, 379.09; 702/101

[56]  References Cited

U.S. PATENT DOCUMENTS

| | | |
|---|---|---|
| 4,307,608 | 12/1981 | Useldinger . |
| 4,333,340 | 6/1982 | Elmeskog . |
| 4,501,148 | 2/1985 | Nicholas . |
| 4,556,216 | 12/1985 | Pitkanen . |
| 4,607,841 | 8/1986 | Gala . |
| 4,702,108 | 10/1987 | Amundsen . |
| 4,742,832 | 5/1988 | Kauffmann . |
| 4,805,455 | 2/1989 | DelGiorno . |
| 4,824,103 | 4/1989 | Smidt . |
| 4,882,677 | 11/1989 | Curran . |
| 4,972,711 | 11/1990 | Jain . |
| 5,275,045 | 1/1994 | Johnston et al. .................. 73/379.01 |
| 5,331,851 | 7/1994 | Parviainen . |
| 5,348,519 | 9/1994 | Prince ................................... 482/6 |
| 5,391,128 | 2/1995 | DeBear ................................. 482/4 |
| 5,621,667 | 4/1997 | Waters ............................... 702/101 |
| 5,800,310 | 9/1998 | Jones . |

Primary Examiner—Glenn E. Richman
Attorney, Agent, or Firm—Boris Leschinsky

[57] ABSTRACT

A muscle strength testing and measuring apparatus contains a bar-like strength testing mechanism slidably placed over a pair of upright posts for adjustment of vertical position and allowing a variety of muscle groups to be tested by the user without any specialized knowledge. The apparatus can be used for physical training before and after exercise as well as for rehabilitation purposes. The position adjustment mechanism includes a jamming cylinder controlled by a link plate, which in turn can be activated by simple lifting or lowering the bar-like mechanism. Piezo-electric tensile sensors are placed in the middle portion of the mechanism to indicate the muscle force which signal is then transmitted to a display unit. Additional pull force strength testing units are placed over the same posts allowing also for adjustment of height position. A great number of configurations are described that can be achieved by easily switching the apparatus from one position to the next.

8 Claims, 5 Drawing Sheets

MUSCLE STRENGTH TESTING APPARATUS

BACKGROUND OF THE INVENTION

1. Field of the Invention

This invention generally relates to an apparatus for testing and indicating the strengths of individual muscles or groups of muscles; and, more specifically, to an apparatus especially well-suited to test and indicate the strengths of individual muscles and the comparative strengths of corresponding muscles. The apparatus can be used successfully in a gym environment for training or rehabilitating purposes.

2. Description of the Prior Art

Over the years, various types of equipment have been developed to objectively and quantitatively measure the strength of individual muscles. As a therapeutic tool, such devices are very helpful in that they help a therapist identify specific muscles that need to be strengthened and to design a program that will help those particular muscles. Moreover, a quantitative measurement will tell not only which muscles are weak, but also how weak those muscles are. Further, as a person is undergoing treatment, an objective measure of the progress he or she is making, first, helps the therapist modify the treatment program, if necessary, and second, allows the patient to witness personally the fact that his or her muscles are getting stronger with therapy, which often encourages the patient to continue the treatment. In addition, often a patient may believe he or she is fully recovered and will discontinue treatment. An accurate, quantitative and objective measure of the strength of each muscle may show otherwise, however, and convince the patient to continue treatment.

As an exercise training tool, an objective and quantitative measurement of the strength of individual muscles will help a person or a trainer develop a highly personalized exercise program that concentrates on the muscles that need the most work. Occasional retesting will enable an individual to observe personally the progress he or she is making, and will help show how effective a particular exercise program is and, if it becomes advisable to do so, how a program should be modified. An individual may test and record the strengths of his or her muscles while healthy to provide a personal standard; and if that person is later injured, he or she, while recovering, can compare his or her muscle strengths against that recorded standard to determine whether the muscles have adequately recovered before resuming a particular activity, thus lessening the risk of a re-injury or of a new injury.

Exercising devices and, similarly, muscle strength testing devices are well known in the prior art. For instance, exercising devices are shown in U.S. Pat. Nos. 1,023,756 (Pons); 4,376,533 (Kolbel); 3,759,514 (Cox); and 4,211,405 (Blowsky et al). These patents disclose various exercising devices utilizing push and pull (compression and tension) operating modes with use limited to exercising upper and/or lower extremities. The patent to Pons shows displacement graduations to provide force or strength indication during exercising. U.S. Pat. No. 3,784,195 (Johnson) discloses a push pull exerciser device having one end attached to a fixed surface and having its other end equipped with a two-hand handle without any provision for measurement of force. U.S. Pat. No. 3,902,480 (Wilson) discloses an electromechanical system that relates substantially only to provision of isotonic or isokinetic motion for exercise training.

U.S. Pat. No. 4,408,183 (Wills) discloses an exercise monitoring device for measuring force, for variously timing force application, and for counting the number of repetitions of particular exercises.

U.S. Pat. Nos. 4,170,225 (Criglar et al); 4,246,906 (Winberg et al); 4,450,843 (Barney et al); and 4,461,301 (Ochs) show a variety of biofeedback devices, not necessarily intended specifically for use in muscle exercising or testing. Biofeedback systems employable in conjunction with muscle training and testing are disclosed in U.S. Pat. Nos. 3,916,876 (Freeman) and 4,110,918 (James et al). U.S. Pat. No. 4,571,682 (Silverman et al) discloses a system for acquisition, various processing, and display of a variety of physiological measures for use in enhancement of skilled performance or behavior.

Additional examples of muscle strength testing and indicating apparatuses can be found in U.S. Pat. Nos. 5,331,851 (Parviainen et al); 4,972,711 (Jain et al.); 4,882,677 (Curran); 4,824,103 (Smidt); 4,805,455 (DelGiorno et al); 4,742,832 (Kauffmann et al); 4,702,108 (Amundsen et al); 4,333,340 (Elmeskog); and 4,307,608 (Useldinger et al).

As indicated above, the prior art shows a number and variety of small and lightweight relatively specialized testing and exercising devices, each having a particular use in either testing or exercising and being applicable to comparatively few groups of muscles. Some devices provide only tension and some only compression facilities while some provide both; others provide for force measurement, yet others offer only qualitative dynamometric indication, etc.

Therefore, the need exists for a more universally-applicable, lightweight and compact multiple-use devices for testing and exercising of most muscle groups of the human body of interest in training and in evaluation of muscle performance and training progress as well as in medical clinical tasks, adaptable both in their interfacing facilities and in their measurement acquisition, handling, processing, and display and other output capabilities in adequately simple manner to permit use without specialized skill, which devices have neither existed nor been suggested heretofore.

SUMMARY OF THE INVENTION

Accordingly, it is an object of the present invention to overcome these and other drawbacks of the prior art by providing a novel muscle strength testing and displaying apparatus designed to indicate the strength of a wide variety if not most major groups of muscles of a human being with easy and fast changes of apparatus configurations.

It is another object of the present invention to provide a muscle strength testing apparatus capable of easy adaptation to users of various size and physical abilities.

It is yet a further object of the present invention to provide a muscle strength testing apparatus for use by a person without any specialized skills.

According to the invention, there is provided a muscle testing apparatus consisting of a horizontal bar-like muscle strength testing mechanism for measuring of applied force. This mechanism is capable of sliding over a couple of vertical posts each containing a position adjustment mechanism between the post and that muscle testing mechanism. Each position adjustment mechanism contains a sliding cylinder designed to jam against the post when tilted by a link plate in turn activated by the movement of the muscle testing mechanism.

The middle portion of the muscle testing mechanism contains a number of tensile sensors such as a piezo-electric sensor. When the user applies force through a clearly marked grip area of the mechanism, the signal from the tensile sensors is transmitted through a computational block to a display unit.

Additionally, pull force testing units are provided on one or preferably both vertical posts that are designed to allow adjustment of their position as well along the posts. Each unit contains a spring-loaded housing and a force displaying gauge activated by pulling on a flexible link such as a cable or a rope. Depressing of a spring via a lever releases the housing and allows repositioning along the post.

For a better understanding of the invention, its operating advantages and the specific objects attained by its uses, reference should be made to the accompanying drawings and descriptive matter in which there is illustrated a preferred embodiment of the present invention.

BRIEF DESCRIPTION OF THE DRAWINGS

A more complete appreciation of the subject matter of the present invention and the various advantages thereof can be realized by reference to the following detailed description in which reference is made to the accompanying drawing in which.

DETAILED DESCRIPTION OF THE MOST PREFERRED EMBODIMENT OF THE INVENTION

Figure 1:
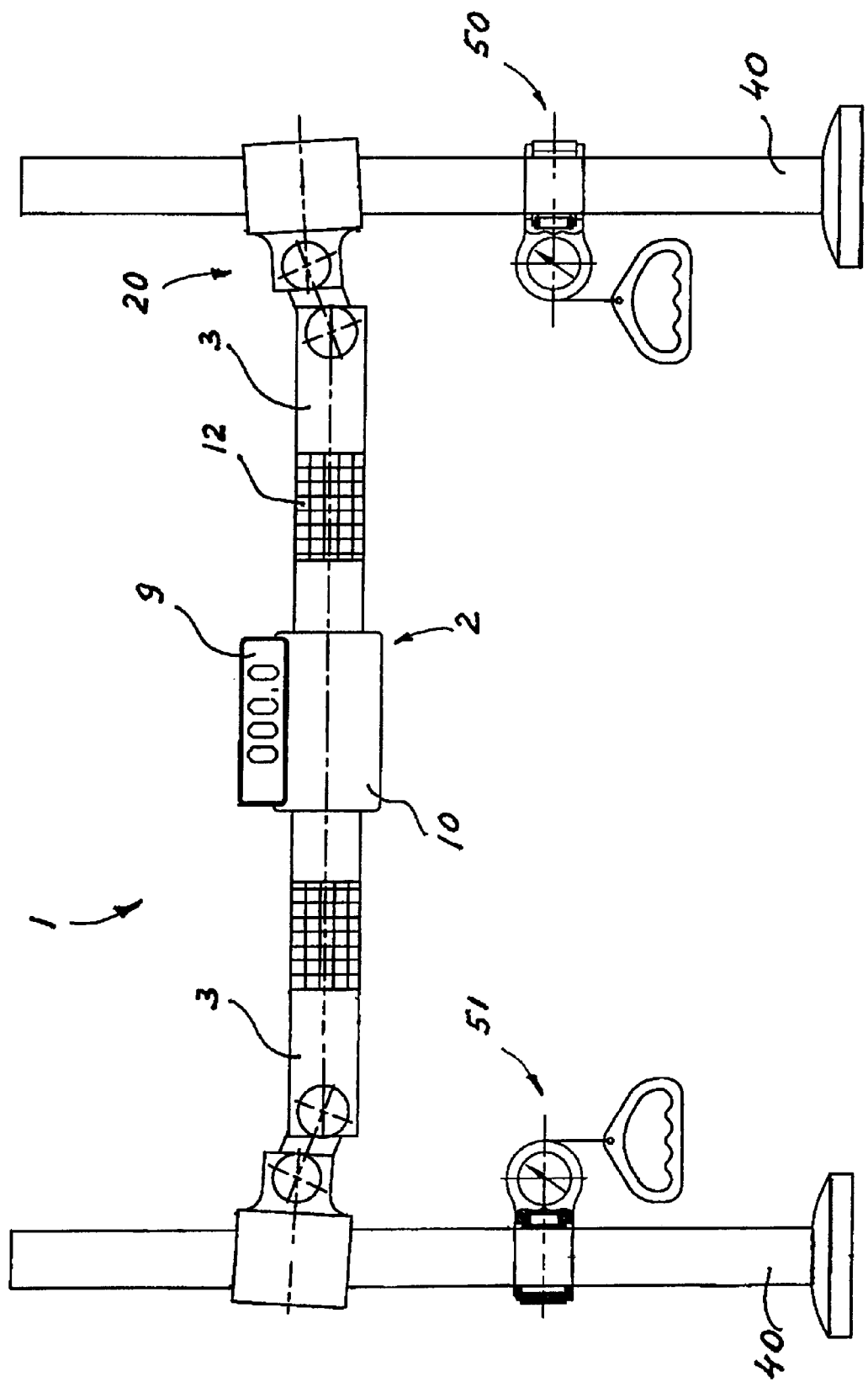
FIG. 1 is a general view of the apparatus of the present invention.

A detailed description of the present invention follows now with reference to accompanying drawings in which like elements are indicated by like reference numerals.

According to the present invention, the muscle strength testing apparatus consists of a bar-like muscle strength testing mechanism (1) slidingly disposed via two identical position adjustment mechanisms (20) about two upright parallel posts (40) as shown on FIG. 1. Posts (40) may be permanently attached to the floor or to a commonly known heavy post bases as shown on the drawing. In addition, each post (40) contains a horizontal force measurement unit (50) and (51) capable of being positioned along the post (40).

Muscle strength mechanism (1) is designed to transform the physical effort of the user into a digital readout of the display unit. It contains two symmetrical pipes (3) and an indication unit (2).

Figure 2:
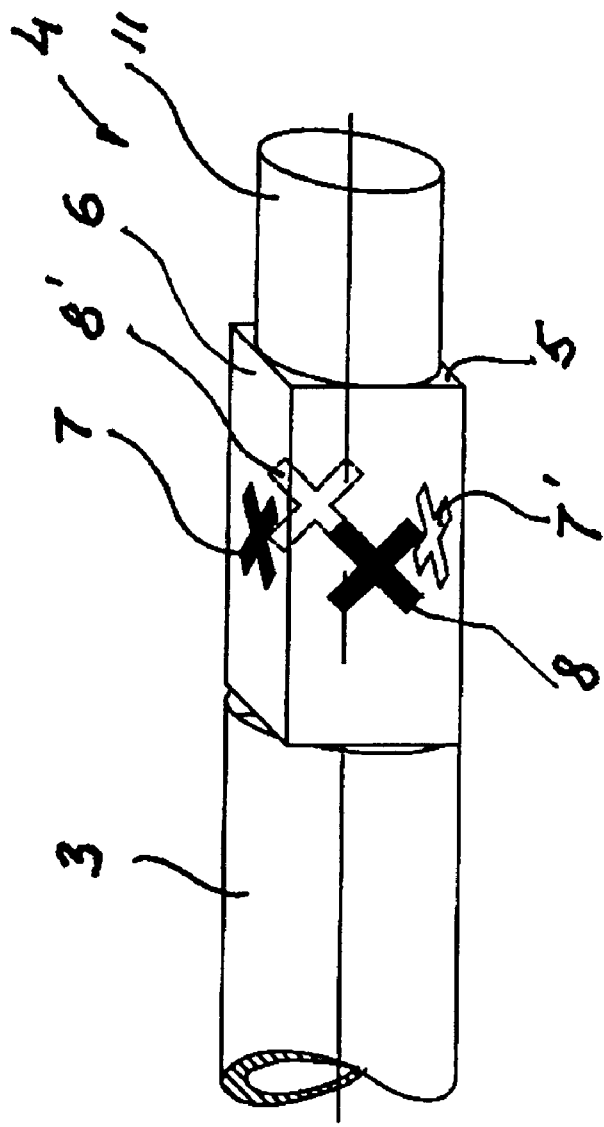
FIG. 2 is a view of the strength sensor unit with some components being removed for clarity of the illustration.

FIG. 2 depicts in greater detail the indication unit (2) as having a housing (4) with a square or rectangular shaped middle portion (5). Each side of the middle portion (5) contains a tension sensor such as a piezo-electrical sensor in such a way that the top (7) and the bottom (7') sensors react to "forward" and "backwards" movements of the mechanism (1) by the user, while the front (8) and the rear (8') sensors react to "up" and "down" movements of the same mechanism (1). All signals from these four sensors are fed through a computation unit of any known design to a display (9) attached to a cover (10) as seen on FIG. 1. For clarity of illustration of FIG. 2, the display unit (9), computation unit and all electrical wires and other supportive structures are not shown. Optional provisions can be made to transmit the information from a display unit to the outside recording device (not shown). Various types of display functions are envisioned for the display unit (9) such as lock on the maximum force, recall of the last number and so on as is usually done for these types of devices.

The housing (4) contains two round side extensions (11) attached to the square shaped middle portion (5). These extensions are designed to accept the ends of the pipes (3) of the mechanism (1). Further along their length away from the center of the mechanism (1), these pipes (3) contain a clearly marked grip zones (12) to indicate to the user the correct position of applying force to the mechanism (1) to insure accurate measurements. The outside ends of pipes (3) engage with the elements of the vertical position adjustment mechanisms (20).

The above mentioned mechanisms (20) are designed to allow easy adjustment and "up" and "down" sliding of the bar-like mechanism (1) along the posts (40) while providing for reliable fixation of it at a desired location. Each mechanism (20) contains a sliding portion (21) hingedly attached by the link plate (22) to the stopper mechanism (23) as shown in greater detail on FIG. 3. In turn, the sliding portion (21) is capable of moving along the post (40) by containing a cylinder (24) with an inside diameter slightly larger then the outside diameter of the post (40). A side bar (25) extends horizontally from cylinder (24) and contains a vertical opening to accept the link plate (22) (not shown on FIG. 3) and a horizontal hole for the axis pin (26) to hingedly connect the sliding portion (21) to the link plate (22).

Figure 4:
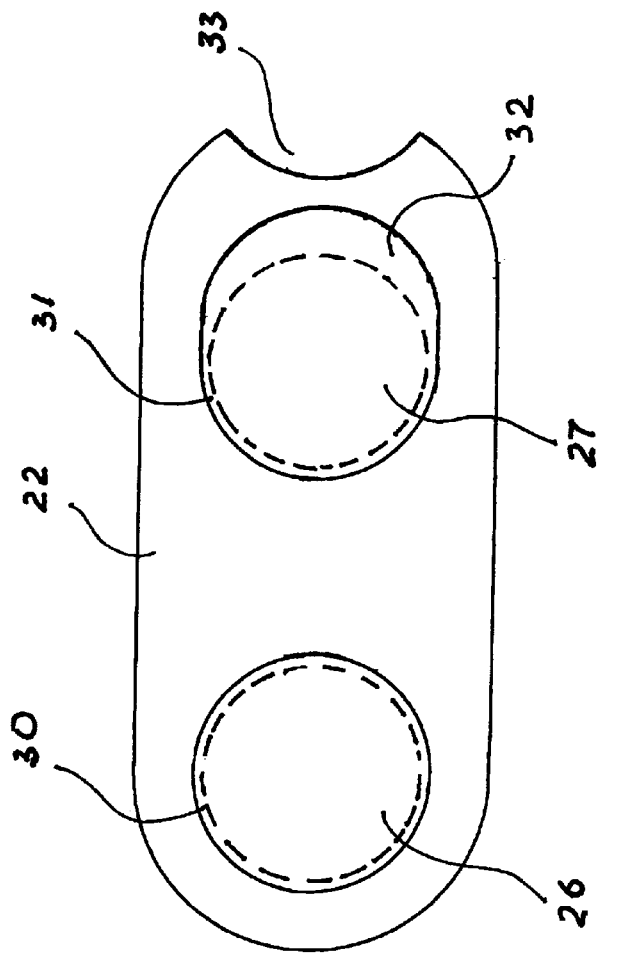
FIG. 4 is an enlarged side view of the link plate of the mechanism shown on FIG. 3.

The stopper mechanism is located at the outside end of the pipe (3) which has a vertical opening designed to accept the link plate (22) and a hole for the axis pin (27) made in the same manner as in the sliding portion (21). In addition, the spring (29) loaded ball (28) is located next to the link plate (22). The link plate (22) itself is shown in greater yet detail on FIG. 4 and contains a round hole (30) to accept the axis pin (26), an oval hole (31) to accept the round axis pin (27) while having a clearance (32), and a round cut-out (33) positioned against the ball (28).

Figure 3:
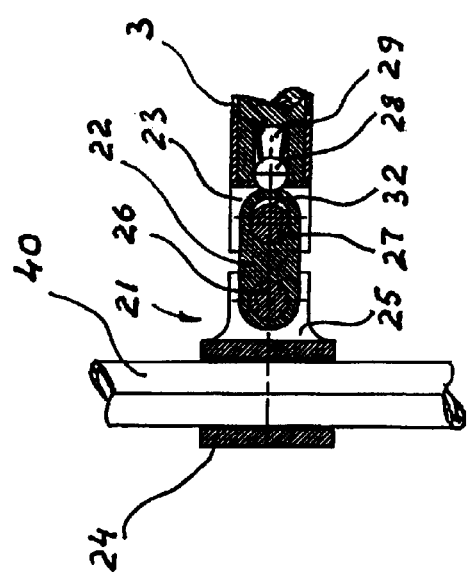
FIG. 3 is a cross-sectional view of the mechanism for vertical position adjustment of the apparatus in an unloaded state.

This design of the vertical position adjustment mechanism (20) allows for easy movement of the mechanism (1) along the posts (40) and fixing it in the desired location. FIG. 3 shows the "neutral" position of the mechanism (20) is which all parts are positioned horizontally so that the ball (28) is forced by the spring (29) to enter into the round cut-out (33) of the link plate (22), followed by the movement of the link plate (22) further away from the display unit (9) and the central portion of the mechanism (1). The clearance (32) is shifted to the outside position as the axis pin (27) is moved closer to the ball (28). That in turn release the cylinder (24) and places it in the vertical position allowing free movement "up" or "down" the post (40). After placing both mechanisms (20) on the sides of the mechanism (1) in this position, slow moving of the mechanism (1) by the user would bring it to the new desired position.

Once in that position, tilting motion of the user in the "up" direction would bring the components of the mechanism

Figure 5:
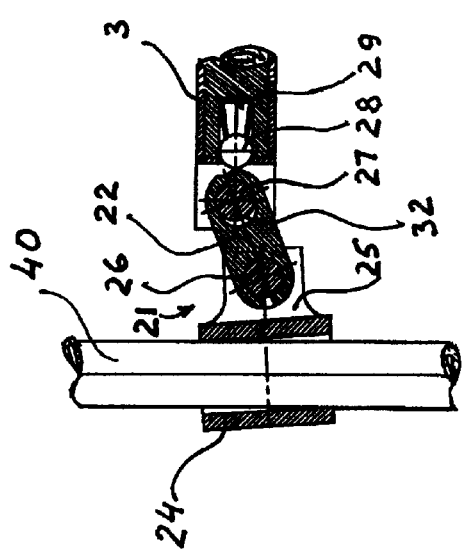
FIG. 5 is a view of the vertical position adjustment mechanism showing all its components during the lifting of the device.

(20) in the position shown on FIG. 5. The ball (28) is now disengaged from the cut-out (33), the axis pin (27) has moved up and pulled with it the link plate (22), which in turn has tilted the cylinder (24) to a "jammed" position thus fixing the mechanism (1) in place) and making it ready for force measurements in the "up" direction. To release the mechanism (1), the user can simply place all components back into the horizontal position. Clicking sound of the ball (28) engaging and disengaging from the cut-out (33) serves as an audible indicator of the configuration of the mechanism (1).

Figure 6:
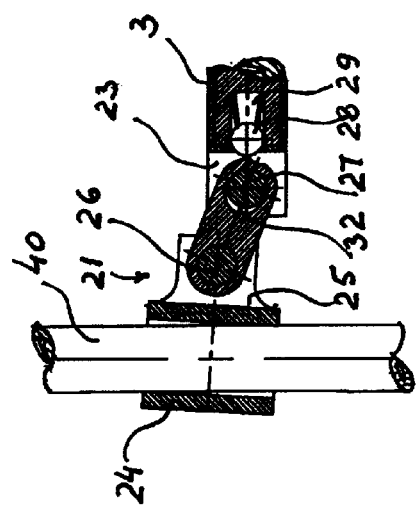
FIG. 6 is a view of the same vertical position adjustment mechanism showing all its components during the lowering of the device.

FIG. 6 shows the stopper mechanism in the reversed position which can be encountered after tilting the link plate "down". A similar interaction between parts leads to the tilted "jamming" position of the cylinder (24) on the post (40) which fixes the vertical position of the mechanism (1).

Figure 7:
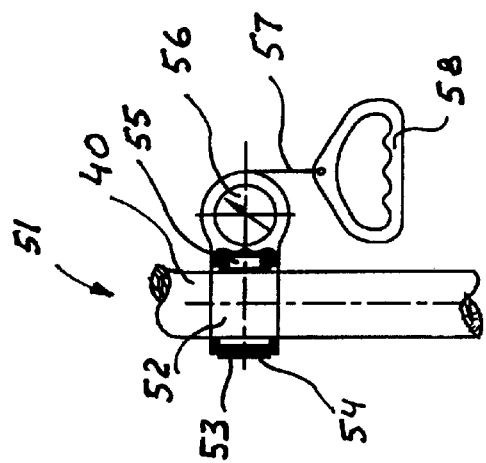
FIG. 7 is a cross-sectional view of the horizontal muscle strength testing mechanism of the apparatus, and finally

In addition to the mechanism (1) allowing to measure the vertical and some horizontal force of the user at positions of various heights, the apparatus of the invention may be equipped with one or two additional horizontal pull force measurement units (50) and (51) which are also slidably disposed on the posts (40) as shown in general on FIG. 1 and in more detail on FIG. 7. Each unit (50) or (51) consists of a cylindrical housing (52) easily slidable over the post (40) and the stopper unit (53) containing the lever portion (54) and a spring (55). Force measurement and display unit (56) of any commonly known design is attached to the housing (52) and is activated by a flexible link (57) with a handle (58). This flexible link (57) can be made of a cable, rope, small chain or other similar material.

Pulling on the handle (58) would lead to the activation of the force measurement unit (56) irrespective of the direction of the pull. At the same time, most applications are envisioned with the horizontal direction being the primary direction of the pull.

Position adjustment of the unit (50) or (51) is achieved by depressing on the lever portion (54) which in turn compressed the spring (55) and disengages it from the post (40) freeing the unit (50) or (51) to be moved to a new location. Once in that location, the user releases the lever portion (54) thus again engaging the spring (55) with the post (40) and therefore "jamming" the unit (50) or (51) in place.

Figure 8:
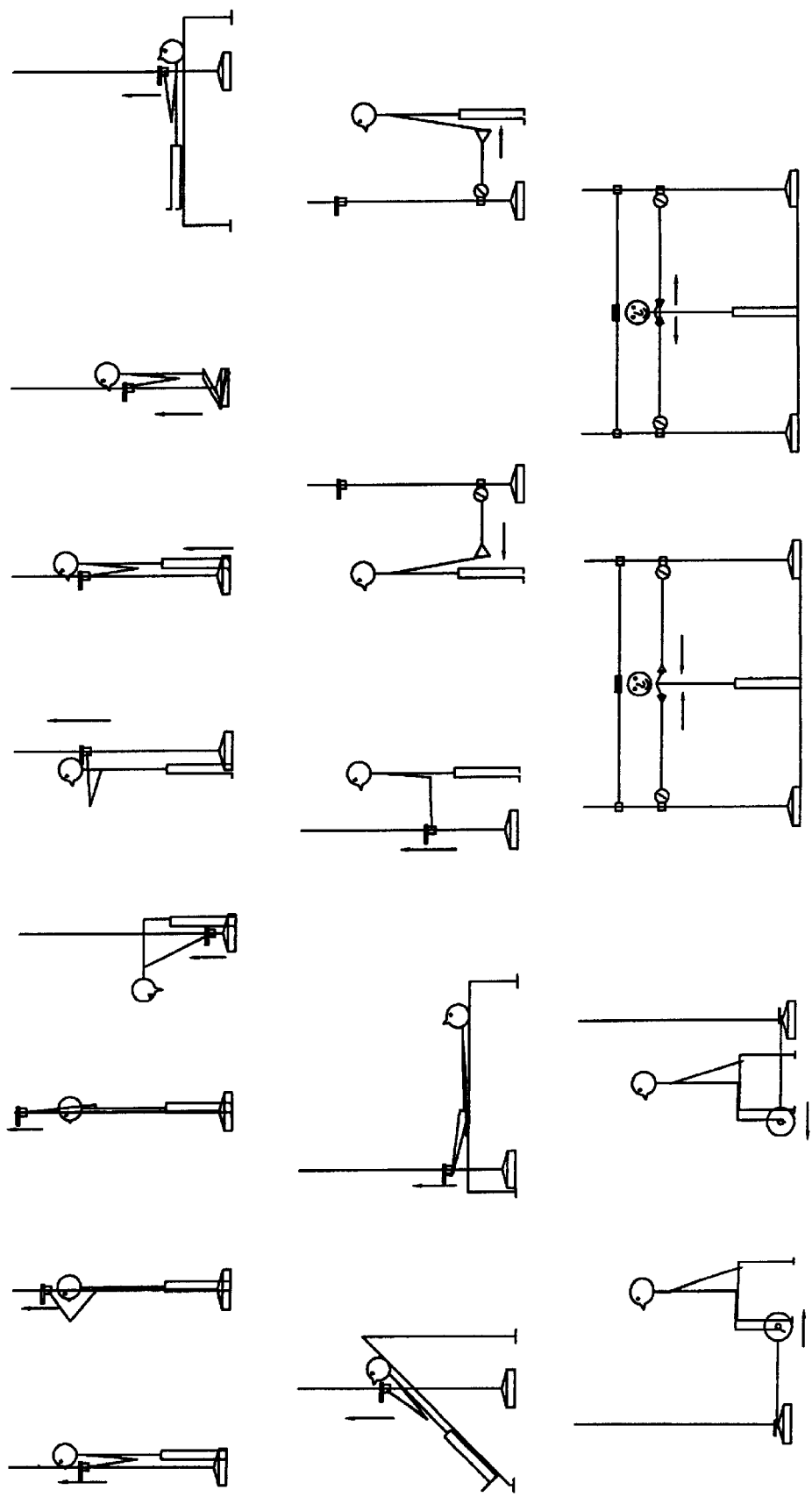
FIG. 8 is a diagram indicating various uses of the apparatus including a variety of user positions in relation to the apparatus.

FIG. 8 illustrates some of the possible configurations of the muscle strength testing and measuring apparatus of the present invention.

Although the present invention has been described with respect to a specific embodiment and application, it is no t limited thereto. Numerous variations and modifications readily will be appreciated by those skilled in the art such as the use of the vertical position adjustment mechanism for other exercise equipment and are intended to be included within the scope of the present invention, which is recited in the following claims.

What I claim is:

1. A muscle strength testing apparatus for measuring and displaying a force applied by a user, said apparatus comprising:
   a first upright post,
   a second upright post, positioned in parallel with the first upright post,
   a first and a second position adjustment means, said means slidingly placed about said respective first and second upright posts, said means having a central opening being larger in size then the size of said first and second upright posts, said openings accepting said respective posts, said means having a "neutral" and a "tilted" position, said means capable of sliding freely along said posts while in said "neutral" position, said means capable of being jammed and fixed in place while in said "tilted" position,
   a first and a second link plate, each plate being hingedly attached to said respective first and second position adjustment means, and
   a bar-like muscle strength testing mechanism having a first end, a middle portion and a second end, said first and second ends hingedly connected to said respective first and second link plates, said middle portion containing a plurality of tension sensors and a display unit for testing and displaying of said force applied to said bar-like mechanism while said first and second vertical position adjustment means being in said "tilted" position.

2. The apparatus as in claim 1, wherein said middle portion of said bar-like mechanism having a square cross-section with a bottom side, a front side, a top side, and a rear side, each side contains a respective tension sensor, whereby said front and rear sensors adapted for testing of said force applied in "up" and "down" directions, said top and bottom sensors adapted for testing of said force applied in "forward" and "backwards" directions.

3. The apparatus as in claim 1, wherein said posts and said openings having a round cross-sectional shape.

4. The apparatus as in claim 1, wherein said bar-like mechanism further comprising clearly marked grip areas, said grip areas located symmetrically about said middle portion.

5. The apparatus as defined in claim 1, wherein said link plates further comprising a round cut-out, said first and second ends further comprising a spring-loaded ball, said ball adapted to engage said link plate when positioned against said round cut-out while said position adjustment means being in "neutral" position.

6. The apparatus as in claim 1, further comprising a pull force testing means slidably positioned about said upright post.

7. The apparatus as in claim 6, wherein said pull force testing means comprising a spring-loaded stopper means placed about said post, a pull force testing means attached to said stopper means, and a flexible link terminated with a handle, whereby said flexible link activating said pull force testing means when said force is applied to said handle.

8. The apparatus as in claim 7, wherein said spring-loaded stopper means comprising a housing slidably positioned about said post, a spring attached to said housing, and a lever for depressing said spring, said spring having an "engaged" position and a "disengaged" position, said spring jamming said stopper means against said post in said "engaged" position, said spring freeing said stopper means against said post while being depressed by said lever and placed in said "disengaged" position.

* * * * *